United States Patent
White

(10) Patent No.: US 7,331,993 B2
(45) Date of Patent: Feb. 19, 2008

(54) INVOLUTED ENDOVASCULAR VALVE AND METHOD OF CONSTRUCTION

(75) Inventor: Jennifer K. White, Brookline, MA (US)

(73) Assignee: The General Hospital Corporation, Boston, MA (US)

( * ) Notice: Subject to any disclaimer, the term of this patent is extended or adjusted under 35 U.S.C. 154(b) by 459 days.

(21) Appl. No.: 10/512,005

(22) PCT Filed: May 5, 2003

(86) PCT No.: PCT/US03/14160

§ 371 (c)(1),
(2), (4) Date: Oct. 18, 2004

(87) PCT Pub. No.: WO03/092554

PCT Pub. Date: Nov. 13, 2003

(65) Prior Publication Data

US 2005/0240262 A1  Oct. 27, 2005

Related U.S. Application Data

(60) Provisional application No. 60/377,721, filed on May 3, 2002.

(51) Int. Cl.
*A61F 2/24* (2006.01)
*B28B 1/00* (2006.01)
(52) U.S. Cl. ..................... 623/2.12; 264/632
(58) Field of Classification Search .................. 600/36; 623/1.24, 1.26, 2.12, 2.19, 901, 909, 910; 264/632, 146
See application file for complete search history.

(56) References Cited

U.S. PATENT DOCUMENTS

| 5,509,930 A | 4/1996 | Love |
| 5,512,046 A | 4/1996 | Pusinelli et al. |
| 5,554,184 A | 9/1996 | Machiraju |
| 5,609,600 A | 3/1997 | Love et al. |
| 5,612,885 A | 3/1997 | Love et al. |
| 5,662,705 A | 9/1997 | Love et al. |
| 5,713,950 A | 2/1998 | Cox |
| 5,755,782 A | 5/1998 | Love et al. |

(Continued)

OTHER PUBLICATIONS

Jennifer K. White, Involuted Cylinder Valve, Fifth Annual NewEra Cardiac Care: Innovation & Technology, Jan. 4-6, 2002, Dana Point, California.

(Continued)

*Primary Examiner*—Ehud Gartenberg
*Assistant Examiner*—Jason-Dennis Stewart
(74) *Attorney, Agent, or Firm*—Fish & Richardson P.C.

(57) ABSTRACT

A prosthetic tri-leaflet valve formed by involuting a portion of a tubular structure inside itself. The valve can be made by a method comprising providing a tubular segment in which three equidistant longitudinal incisions are made in one end of the tube creating three flaps which are involuted, i.e., folded, in toward the inside of the tube and the edges of the flaps secured to the inner wall of the tube to form leaflets. The tube can be formed of a single sheet of synthetic, organic or biological material and can be solid, woven, braided or the like. A braided configuration permits the valve to be annularly compressed and delivered to the site using a minimally invasive delivery mechanism, then expanded at the implantation site.

22 Claims, 9 Drawing Sheets

U.S. PATENT DOCUMENTS

| | | |
|---|---|---|
| 5,961,539 A | 10/1999 | Northrup, III et al. |
| 6,126,686 A * | 10/2000 | Badylak et al. ............ 623/1.24 |
| 6,241,763 B1 | 6/2001 | Drasler et al. |
| 6,270,526 B1 * | 8/2001 | Cox .......................... 623/2.12 |
| 6,334,873 B1 | 1/2002 | Lane et al. |
| 6,342,069 B1 | 1/2002 | Deac et al. |
| 6,358,277 B1 | 3/2002 | Duran |
| 6,494,909 B2 | 12/2002 | Greenhalgh |
| 6,673,109 B2 * | 1/2004 | Cox .......................... 623/2.12 |
| 6,719,787 B2 * | 4/2004 | Cox .......................... 623/2.12 |
| 6,736,846 B2 * | 5/2004 | Cox .......................... 623/2.12 |

OTHER PUBLICATIONS

Jennifer K. White et al., The Involuted Cylinder Valve: An Aortic Valve Constructed From Pulmonary Artery Trunk, Programme & Abstracts, Stentless Bioprosthesis Fourth International Symposium, May 3-5, 2001, San Diego, Cal.

* cited by examiner

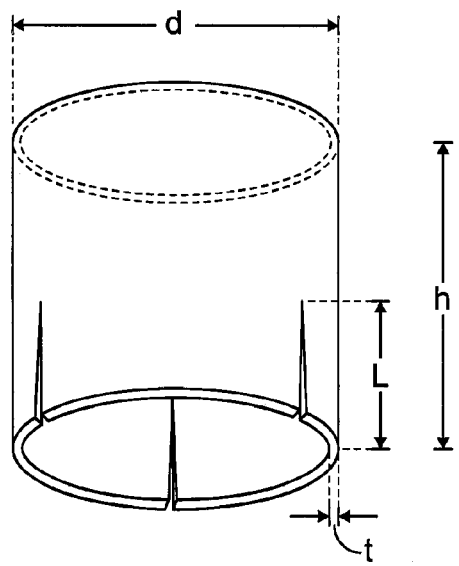 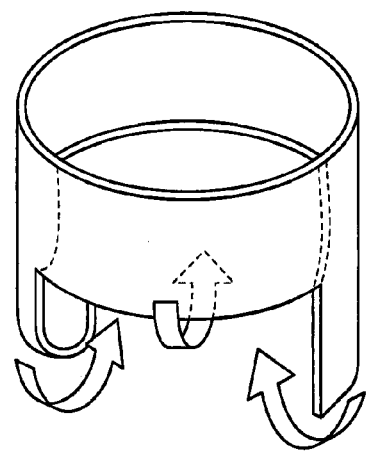
FIG. 11    FIG. 12
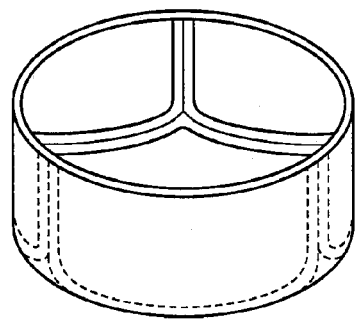 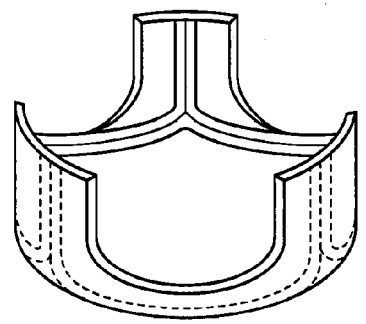
FIG. 13    FIG. 14

INVOLUTED ENDOVASCULAR VALVE AND METHOD OF CONSTRUCTION

CROSS-REFERENCE TO RELATED APPLICATION

This application is a national phase application of, and claims priority from, International Application No. PCT/US03/14160, filed May 5, 2003, under 35 U.S.C. 371, which claims the benefit of priority from U.S. Provisional Patent Application No. 60/377,721, filed on May 3, 2002. The entire contents of both applications are incorporated herein by reference.

FIELD OF THE INVENTION

The present invention relates to a prosthetic valve with an involuted structure. The present invention also relates to methods and apparatus for constructing an involution valve.

BACKGROUND OF THE INVENTION

Since the implant of the first cardiac valvular prosthesis in the anatomic position in 1960, more than 50 different cardiac valves have been introduced over the last forty years. Unfortunately, after years of development of mechanical and tissue valves there remain significant problems associated with both types of valves.

Mechanical vs. Tissue Valves

Mechanical valves are durable in patients but require long-term anticoagulation therapy. Tissue valves offer freedom from anticoagulation therapy and the problems of bleeding, but tend to degenerate rapidly, particularly in younger patients. The most commonly implanted tissue valves are constructed from chemically-treated animal tissues (i.e., glutaraldehyde-fixed pericardial or porcine valves). The preservation, sterilization, and fixation processes currently used in tissue valve preparation are believed to contribute to the lack of longevity of tissue valves.

Ross Procedure

One alternative approach for aortic valve replacement has been to transpose the patient's own pulmonary valve into the aortic position in the same individual, as described by Ross in the late 1960's. Although a technically demanding procedure, the Ross procedure frees the patient from anticoagulation therapy and has substantial longevity compared to other types of tissue valves. A disadvantage of using the pulmonary valve to replace the aortic valve in the same patient is that the pulmonary valve must also be replaced. Most commonly, the replacement tissue for the excised pulmonary valve is a valve (aortic or pulmonic) derived from a cadaver ("homograft"). Problems arise from lack of donor availability and size mismatches between the donor homograft and the living recipient. Unfortunately, replacing the pulmonary valve with a homograft is associated with immunologically-mediated stenosis in some patients which limits their longevity.

Monocusp Procedure

Alternatively, a single flap of tissue from the pulmonary trunk has been used to create a pulmonary "mono-cusp" valve in pediatric patients undergoing the Ross procedure. Long-term function of the monocusp valve has yet to be documented. Historically, it is known that a single leaflet valve design has a less efficient closure than a tri-leaflet valve. The suboptimal function of a monocusp valve may adversely impact long-term results. It is a drawback that the mono-cusp procedure is restricted to replace a valve at the location where the tissue flap is created. The monocusp procedure does not provide a source for replacement of valves other than the pulmonary valve.

Trileaflet Valve Derived from Pulmonary Artery Tissue

Another previously described method to replace the aortic valve entails surgical reconstruction of a tube of tissue from the pulmonary artery of the same individual. In this procedure, a tube of tissue was harvested from the pulmonary trunk and reconfigured into a trileaflet valve. In order to create a valve, the base of the pulmonary tissue tube was sutured to the aortic annulus and to the aortic wall at three points. This procedure was attempted in three pediatric patients and abandoned due to immediate and severe aortic insufficiency in two patients. The failure of this valve replacement procedure resulted, in part, from the extreme technical challenge for the surgeon. In this procedure, the surgeon must simultaneously construct and implant the valve while attempting to surgically compensate for any size discrepancies between the donor tissue and the recipient valve site.

As described previously, promising attempts to create a tissue valve by reconfiguring an individual's own living tissues have been problematic. It would be advantageous to have a method to more efficiently, effectively, and reliably construct a functional and durable tissue valve. It would be desirable for the valve to be a non-immunogenic structure capable of cellular regeneration and repair.

U.S. Pat. No. 5,713,950, issued to Cox discloses a valve constructed from a tubular structure. This invention is a nesting of tubes dependent on multiple suture lines or points to join the tubes to create a valvular structure. It is a drawback that these sutures are positioned in areas of high stress during the function of the valve through the cardiac cycle. Although this valve is a simple design, it would be inefficient and difficult to use this method to reconfigure the patient's own tissues into a valvular structure.

U.S. Pat. No. 6,494,909, issued to Greenhalgh, discloses a device and means for a braided valve and minimally invasive deployment. The invention does not describe the area of attachment of the leaflets to the walls of the tubular structure to create a functional three-dimensional tri-leaflet valve. This invention does not describe a means for creating an autologous or living tissue valve. It is a further disadvantage that this invention describes that it is placed in a catheter for deployment. This is distinguished from other braided structures which are deployed by an internal mechanism with the potential for more maneuverable and narrower insertion profiles (such as that disclosed in Patent Cooperation Treaty application (designating the U.S.) No. PCT/US02/40349, filed Dec. 16, 2002, entitled "DYNAMIC CANNULA," and commonly assigned to the assignee of the present invention, the disclosure of which application is incorporated herein by reference in its entirety).

SUMMARY OF THE INVENTION

In one exemplary embodiment, the present invention provides for constructing a prosthetic valve by a technique referred to interchangeably as the "involuted cylinder" or "involution" method. The involution valve may be constructed of synthetic, semi-synthetic, organic or biological material or mixtures or combinations thereof. The valve is efficient to construct, may be derived from the patient's own tissues, and is particularly suitable for replacement of aortic or pulmonic valves.

In one exemplary embodiment, the present invention provides a valve constructed of a tubular structure involuted inside itself. The three-dimensional shape of the "involution valve" may be provided by folding, braiding, weaving, knitting, or combinations of these operations on the material.

The material may be biological, synthetic, semi-synthetic, organic, or a combination of these materials. The patient's own tissue (e.g., pericardium, pulmonary artery, or aortic tissue) can be reconfigured into a functional valve using this method. Some examples of material sources include, but are not limited to, tissue derived from the same individual (e.g., pericardium, aortic, or pulmonary artery tissue) or a different individual of the same species (e.g., cadaver tissue) or a different species (e.g., decellularized porcine small intestinal submucosa).

The valve may be a scaffold, matrix, or other structure that undergoes a maturation process of living autologous cell deposition thereon. For the purposes of the present disclosure, the term scaffold will be referred to in an exemplary, but nonexclusive, manner. An example of a potentially suitable scaffold substance is decellularized porcine small intestinal submucosa. The scaffold could provide signaling to cells to organize as an autologous valve, provide a support structure for cell organization, or function as a non-immunogenic valve regardless of cell population. The scaffold can be a permanent, semi-permanent, or temporary structure capable of resorption or remodeling. In this manner, the valve would, when implanted and the patient adapted, have a lack of exposed immunogenic material.

The present invention provides a method of forming a valve or valve scaffold, comprising, in one exemplary embodiment: (1) providing a tube of material, (2) involuting the tube inside itself, (3) selectively attaching portions of the inside tube to the outer tube of material, (4) implanting the valve in a patient.

Accordingly, it is a feature of the present invention to provide a valve that has minimal immunogenic structure.

It is another feature of the present invention to provide a valve that is capable of cellular regeneration and repair and that is functional and durable.

Other features and advantages of the present invention will become apparent upon reading the following detailed description of embodiments of the invention, when taken in conjunction with the appended claims.

BRIEF DESCRIPTION OF THE DRAWINGS

The various features and advantages of the invention will be apparent from the attached drawings, in which like reference characters designate the same or similar parts throughout the figures, and in which:

FIG. 11 shows a perspective view of a cylinder with three equidistant incisions to create flaps or "leaflets";

FIG. 12 shows a perspective view of involution of the flaps inside the cylinder to create leaflets;

FIG. 13 shows a perspective view of an exemplary embodiment of an involution valve showing attachment of the leaflets to the inner side of the outermost tube with "U" sutures;

FIG. 14 shows a perspective view of the involution valve depicting scalloping of the outermost wall to allow for subcoronary implantation and preservation of the Sinuses of Valsalva;

DESCRIPTION OF THE INVENTION

Figure 1:
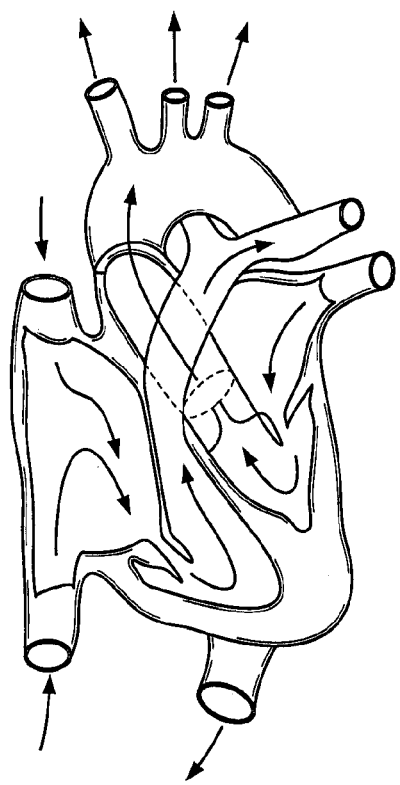
FIG. 1 shows a cutaway view showing an exemplary embodiment of an involution valve of the present invention implanted in the aortic valve position on the left (systemic) side of the heart.

The present invention generally provides a prosthetic valve formed by involuting a tubular structure inside itself. The present invention also provides methods of forming an involution valve.

Primary Structure: Synthetic, Organic, and Biological Materials

In one exemplary embodiment of the present invention an involution valve is formed of synthetic or processed organic material. The material can be any of a number of different biologically inert materials. The following materials are set forth by way of illustration only and are not intended to be exclusive.

Synthetic Materials

Polyglycolic acids (PGA) can be used as non-woven mesh, having high porosity, good cell attachment, good growth and extracellular matrix formation, rapid bioabsorption, and biocompatibility. Examples of materials include, but are not limited to, polyhydroxyalkanotes (PHA or PHO); poly-4-hydroxybutyrates (P4HB) (PHA and P4HB have the properties of elasticity, mechanical strength, thermoplasticity, and have demonstrated increase in cell attachment during seeding with increased collagen development); PGA and P4HB hybrid in the form of thin PGA coated with P4HB to reduce stiffness but provide mechanical strength; absorbable and nonabsorbable suture materials, polylactic acid (PLLA); polycaprolactone; fibrin-gels (moldable); hydrogels (polyethylene glycol-based hydrophilic substances); dacrons; metals, or nitinols particularly biodegradable nitinols); mixtures and/or combinations thereof and the like.

Organic Materials

The valve may also be constructed of polymer-based substances; examples include, but are not limited to, polypropylene, polyester, silk, nylon, plastics, rubbers, silicones, papers or other suitable cellulose based product, polytetrafluoroethylenes (PTFE's), polyurethanes, mixtures and/or combinations thereof and the like.

Biological Materials

Pericardial tissue, arteries, veins, portions of the gastrointestinal tract, combinations of the forgoing and the like can be used. The material can be a chemically-treated tissue such as glutaraldehyde-fixed pericardium or other suitable tissue.

Tissue can be harvested, isolated (for example, a segment of tubular blood vessels such as the autologous pulmonary artery trunk, left or right pulmonary artery, and aorta), created (cell cultures) or tissue engineered (for example, cells populating a scaffold). The living material can continuously bathed in, for example, cell culture medium or Hank's solution so as to retain viability. Tissue sources include autologous (self) tissues, xenograft (e.g., decellularized animal tissues) or allografts (e.g., cadaver tissue). More specific examples of these include decellularized porcine small intestine submucosa ("SIS") and segments of a decellularized aorta, or vena cava tissue from cadaver donors. An example of a decellularization process is incubation of in trypsin/EDTA for 48 hrs to extract endothelial cells and myofibroblasts.

In one exemplary embodiment, the scaffold is decellularized porcine small intestinal submucosa which is reconfigured into a valvular structure, implanted into the individual, and allowed to mature by populating with autologous cells. Population of the scaffold with autologous cells can occur outside (e.g., in pulsatile cell culture "bioreactor") or inside the body (e.g., following implantation). Exposing the cell-populated scaffold to mechanical stresses has been shown to physically signal the cells to produce extracellular matrix material. The mechanical stresses may influence the mass, directionality, strength, and types of biomolecules (e.g., collagen) and cells integrating with the scaffold.

The materials described previously, as well as others, may be used to create a functional three-dimensional valve or scaffold using a method of the present invention. The valve is then implanted into the body, and depending upon the material and the configuration, allowed to mature by healing, endothelialization, autologous cell seeding, and extracellular matrix deposition Secondary Structure: Homogeneous, Non-Homogenous, and Porosity, and Layering Homogeneous The texture or surface structure of the valve material is significant and may be homogeneous or non-homogeneous. Human heart valves and the entire human endovascular system is lined with a smooth homogeneous layer of endothelial cells which serve a multitude of functions, including the prevention of thrombus formation. The material for the present invention may be living tissue such as blood vessels from the patient. In this case, the valve's surface is lined, in part, with a homogeneous layer of endothelial cells.

Other parts of the involution valve, such as an adventitial layer, which are exposed to the endovascular space, may pose a risk to form thrombus. In time following implantation, the non-endothelialized surfaces have the potential to be populated with a homogeneous layer of endothelial cells In most instances, it is preferable for the valve to be substantially completely lined with a smooth homogenous layer of endothelial cells on all surfaces that contact blood. Temporary systemic anticoagulation therapy in this patient during the endothelization period may reduce or eliminate the risk of thrombus formation. Alternatively, chemicals, drugs, growth factors and other agents that promote endothelization and retard thrombus formation may be bound to the valve material to provide local therapy.

Figure 2:
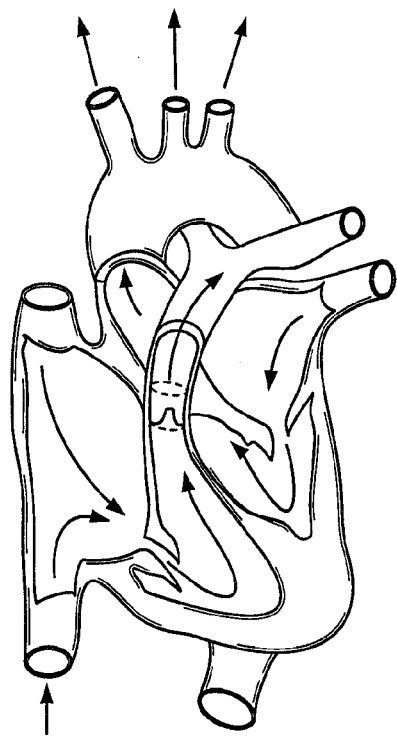
FIG. 2 is a cutaway view showing the involution valve implanted as a pulmonic valve replacement on the right (pulmonic) side of the heart.

In another case, the starting material for valve construction is pericardial tissue which has a smooth side (faces the heart's surface) and a rougher side of collagen and other constituents. Despite the homogenous nature of each side of these materials (e.g., human blood vessels or pericardium), the involution valve may be preferentially constructed such that the smooth side is the diastolic surface and the rough side faces the systolic side of the blood flow during the cardiac cycle. It appears to be advantageous to have the valve involuted such that the most homogeneous, smooth, endothelialized surface is facing the diastolic side of the circulation. This follows from the previous observations of others that tissue valve material undergoes degenerative changes and tends to form thrombus on the diastolic side versus the systolic side of the leaflets. The anatomical orientation in the circulation of the present invention as an aortic valve replacement is depicted in FIG. 1 and is described further in Example 1. A pulmonic valve substitution with the involution valve is shown in FIG. 2 and described in more detail in Example 2. The involution valve may also be suited in other anatomical positions such as for replacement of a mitral or tricuspid valve. The present invention may also serve as a treatment for aortic insufficiency with implantation of the involution valve in the descending aorta.

Non-homogeneous

Figure 3:
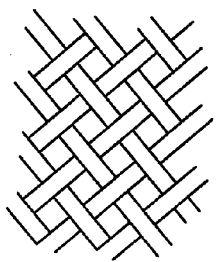
FIG. 3 shows material in a braided configuration.
Figure 4:
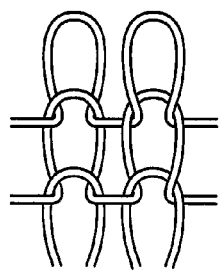
FIG. 4 shows material in knitted configuration.
Figure 5:
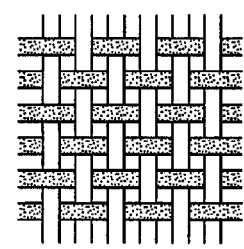
FIG. 5 shows material in a woven configuration.

The material of the involution valve may also be non-homogeneous. For example, the material can be provided as a laminate, mesh, knit, woven or nonwoven material, braids, strands, combinations thereof and the like. Meshes, braids (FIG. 3) knits (FIG. 4), and weaves (FIG. 5) can be formed from interlocking, interlacing, or interweaving connecting fibers of scaffold materials. (e.g., strands of arteries, veins, or other autologous tissues woven, knitted, or braided into a sheet or cylinder);

These materials and fabrication methods may be exploited for their physical characteristics. For example, rib knit may be useful given its property of elasticity in its width direction. Jersey knit is known to have good wrinkle recovery and excellent drape. Double knits are known to be strong since production of the material is carried out on a circular-knitting machine with two sets of perpendicular needles. The physical characteristics of these materials and fabrication techniques may be exploited in light of the anatomy of the native human valve to construct a valve replacement with desirable elasticity, wrinkles, and strength properties.

Consider that the histology of the human native semilunar valves is referred to as highly anisotropic (i.e. not the same in all directions). It follows that the biomechanics of the "cusps" or "leaflets" are not the same in each direction. The leaflets are known to have gross wrinkles or "corrugations" of collagen fibers which expand perpendicular to the cuspal free margin (i.e. radial direction) and imparts a high compliance on the leaflet in this direction. The less compliant "crimp" or "pleat" in the collagen in circumferential direction is a predominate load bearing element, restricting leaflet during filling and cusp distention Strength is provided by groups of collagen cords radiate from the commissures (attachment points of leaflets to wall). These structural features enable the cusps to be pliable when the cusps are unloaded and the heart is contracted (systole), but inextensible when a load is applied during cardiac filling (diasole).

It may be advantageous to impart the physical properties of the human native valve to the present invention. For instance, one could purposefully choose a rib knit or jersey knit configuration of the material along the radial or circumferential direction of the valve construct in order to impart elasticity or draping characteristics to the leaflets. Imparting compliance to the valve leaflet has the potential to dissipate the force imposed by the cardiac cycle on the valve. This may increase strength and durability to the valve following implantation.

In prior studies of others, tissue engineered valve scaffolds have selectively populated with extracellular matrix material when stresses, such as imposed by the cardiac cycle, were mimicked in vitro. As exemplified, the selective use of the materials and fabrication techniques may be used to control the compliance and strength of the valve of the present invention. Controlling the physical properties of the materials and fabrication methods in this manner has the potential to more accurately signal the extracellular matrix materials and the cells that produce them to populate according to conditions that more precisely model the native system.

Strands or fibers of material may be elastic or nonelastic. The fiber diameter can vary in the same or in different fibers composing the material. One study using polyglycolic acid as a scaffold material in valve construction, advocated a fiber diameter of 12-15 µm. In certain cases, fiber diameter can be custom-extruded. The fiber may be rectangular, round, or twisted around itself in a clockwise or counterclockwise position. Each fiber could be a bundle of smaller diameter fibers.

Pores

Porosity of the scaffold material may be significant. The pores or spaces in the material may purposefully be sized to retard thrombus formation and promote endothelization and adhesion of circulating autologous cells. The scaffold materials themselves may be rough or smooth and the pores between them can form smooth shapes or shapes with sharp angles. Variables include pore shape, pore size, open or closed qualities, interpore connectivity, and pore wall morphology. Pores can be the spaces in a weave, braids, or knits. Pores can be introduced into the material by a variety of different techniques, including, but not limited to, cell opening agents and mechanical aperturing. The pores or spaces in the material may purposefully be sized to retard thrombus formation and promote endothelization and adhesion of circulating autologous cells.

In another instance, materials used to construct the valve could change their homogeneous properties and pore size. For example, if one constructed a weave of strands of decellularized porcine small intestal submucosa material, the hydrophilic nature of the material is such that it may form smaller pores and a more homogeneous structure after hydration or implantation in the body.

In certain substances, complex pore geometry (e.g., honeycomb shaped pores) can be created by dispersing paraffin spheres in the dissolved scaffold material (e.g., PLLA and PGA). The paraffin is subsequently dissolved to create pores in the scaffold material. Another technique is to use salt-leaching/sugar crystals/glass crystals to yield a porous matrix. The size of the pores can homogeneous (PGA) or heterogeneous (PLA). The scaffold pore sizes can range from approximately 100-500 microns, more preferably in the 100 to 240 micron range. Other investigators using PLA and PGA scaffolding have noted a decrease in compressive modulus for smaller pore sizes (100-200 microns) as compared to large pore sizes (250-350 or 420-500 microns).

Figure 6:
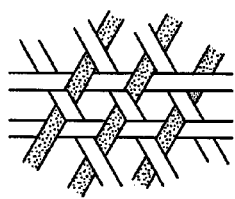
FIG. 6 shows material in a triaxial weave.

The pores in the material or the orientation of spaces between the materials can be purposefully used to impart strength or elasticity to the valve. For example, a triaxial weave is a process of weaving three strands of material at 60 degree angles to one another (FIG. 6). The resulting material has limited or no stretch or distortion in any direction. If equal size and number of strands are used in all three directions, the final material approaches equal strength and stiffness in all directions.

Layering

Figure 7:
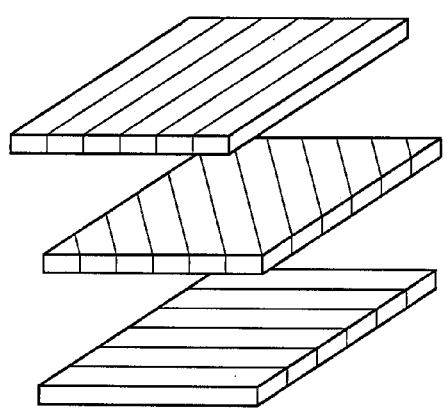
FIG. 7 shows a perspective view of multi-directional layering of materials.

The valve materials can be single or multi-layered. The layers can be orientated such that the directionality of the materials is parallel, perpendicular, or angled. For example, the material may be "biased", "radial", or a combination ("biased/belted") such as that used in automobile tire construction. In a bias construction the material is laid alternating at bias angles of 25 to 40 degrees to the surface layer direction. In a radial design a layer is 90 degrees to the surface material direction. Between these layers can be a series of alternating layers at low angles of 10 to 30 degrees to the surface direction. A combination of these may also be used. The directionality within each layer and orientation of the layers in respect to one another may be used to selectively impose strength and elasticity to the valve (FIG. 7).

It is known from prior anatomical studies that the human semilunar valve leaflet consists of three histologically distinct layers; the ventricularis, the spongiosa, and the fibrosa. The ventricularis faces the inflow surface and consists of mostly collagen "corrugations" with radially aligned elastic fibers. The spongiosa is composed of loosely arranged collagen and glycoaminoglycans. The fibrosa opposes the outflow surface is mainly circumferentially arranged, "crimped," densely packed collagen fibers, mostly parallel to the free edge of the leaflet. With this in mind, the present invention could be constructed of layering material purposefully arranged. For example, the top layer (the future inflow surface of valve leaflet) may be compliant in the radial direction and the most bottom layer could have a directionality perpendicular to the top layer, imparting less compliance in the circumferential direction. A middle layer could be sandwiched in between which has an multi-directional, oblique, or loosely arranged material.

Figure 8:
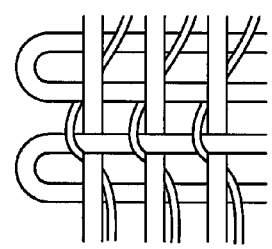
FIG. 8 shows material in a full Leno weave.

Investigators have expressed concern that the use of layering, and in particular, lamination of porcine small intestinal submucosa, may delaminate inappropriately following implantation. One way to overcome this would be to weave, knit, or braid the material to prevent delamination. A specific example is the use of a Leno weave in which the strands are arranged in pairs with one twisted around the other between other strands (FIG. 8). This weave imparts firmness and strength to the material and prevents slippage and displacement of the strands. Alternatively, in certain instances, layering could be avoided by weaving, knitting, or braiding from a single layered strand.

Tertiay Structure: Tubes, Sheets, and Sleeves

Figure 9:
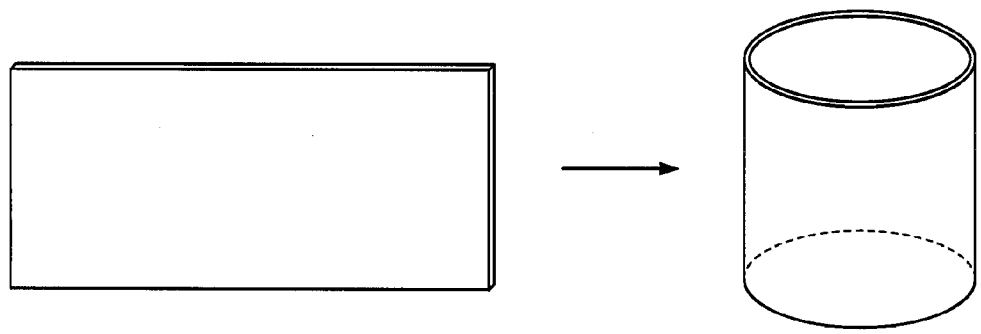
FIG. 9 shows a perspective view showing a cylinder formed from a sheet.

The scaffold can be formed according to the following exemplary method. A quantity of material is provided as a tube or as a sheet. If it is provided as a sheet, two opposing sides are joined together to form a tube by any of a number of techniques known to those skilled in the art and appropriate to the material being used, such as, but not limited to, weaving, interlacing, braiding, knitting, punching, tufting, laminating, suturing, stapling, gluing, welding, fusing, combinations thereof and the like (FIG. 9). The sheet can be knitted, woven, or braided from strands of material. A tubular or cylindrical structure can be created by sleeving techniques using braiding, knitting, weaving or combination of these methods. The structure can be a proper cylinder (the term cylinder and tube being used interchangeably in the present disclosure) or a slightly conical segment. The thickness of the scaffold cylinder can range from about 0.3 mm to 1.0 mm, although it may be thinner or thicker.

Figure 10:
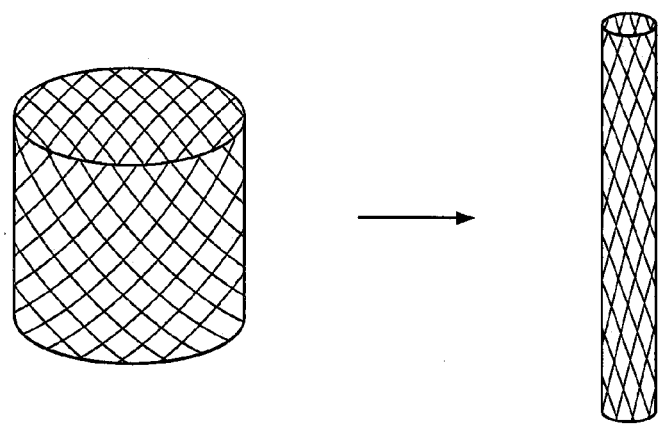
FIG. 10 shows a perspective view of a collapsible braided cylinder.

One advantage of a tubular braid configuration is the possibility of creating a tubular valve that is collapsible (FIG. 10). Braided tubes can be constructed which reduce diameter significantly when a longitudinal force is exerted on the tube. In one instance the diameter of the tubular valve can be reduced in diameter, introduced into the endovascular space in minimally invasive manner, and deployed into a larger diameter structure at the valve replacement site (see Implantation section herein).

Quaternary Structure: Involution, Attachment, Interleaflet Triangles, Sinuses, Leaflet Modifications, and Stents Involution Creating leaflets by involution allows the material at the site of the infolding (i.e., the base of the valve) to retain its compliant nature. This may improve valve durability by facilitating the transfer of stresses and strains on the leaflets to the wall of the implant site (e.g., aortic root). Since the valve is created prior to insertion, it can be tested prior to use and the valve function is not wholly dependent on surgical implantation techniques.

In one geometry of the involution valve shown in FIG. 11, the height "h" of the cylinder 12 is approximately equal to the diameter "d" of the valve implantation site (annulus diameter). Approximately half of the cylinder wall height form the leaflets which span half the diameter of the annulus. The remaining half of the cylinder wall forms the height of the commissures. The height of the commissures is based on the anatomical relationship of annulus to sinotubular junction distance verses annulus diameter in same patient, i.e., height of commissures is approximately half the annulus diameter. The material has a thickness "t".

In one exemplary embodiment, three longitudinal incisions about 120 degrees apart are made in the cylinder to create three flaps of tissue. Preferably, though not mandatorily, the length "L" of the incision is approximately one half the height of the tissue cylinder height "h" less about twice the tissue thickness "t"; i.e., L=½h−2t. The length "L" of the incision should preferably be less than half the height "h" of the cylinder in order to eliminate a potential hole in the base of the valve caused by the incisions.

As shown in FIG. 12 the cylinder is involuted into itself such that the innermost wall (in this case, the three flaps) become the "leaflets" of the valve and the outermost wall becomes the site of attachment to the implantation site. The leaflets are secured to the inner side of the outermost wall (FIG. 13). If the valve construct is intended to be implanted in the aortic valve position, the outermost wall of the valve construct may be scalloped to allow for subcoronary implantation (FIG. 14).

In particular, with tubes of tissue such pulmonary artery, the longitudinal incisions in the cylinder release the constraints on the material and allow the flaps to be easily involuted and secured to the inner wall of the cylinder. Although, the incisions are not necessary, they allow each flap to be secured to the wall independently and may help the leaflets move distinctly from one another during the cardiac cycle. In addition, the perpendicular attachment of each leaflet edge to the wall may facilitate proper tissue repair and growth at each commissure. The presence of incisions at the commissure sites may promote healing and collagen deposition at the commissures.

Figure 15:
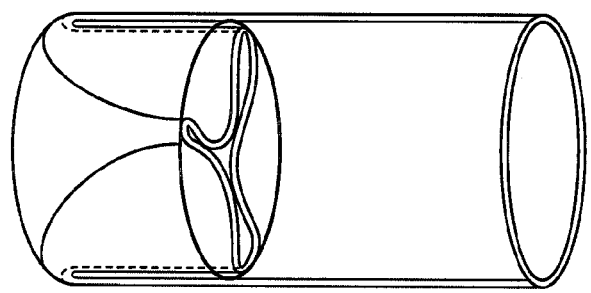
FIG. 15 shows a perspective view of an exemplary embodiment of an involution valve constructed by involuting the tube inside itself without incisions to create flaps.

In another embodiment, no incisions are made and the tubular structure is simply involuted inside itself and selectively attached to the outermost wall (FIG. 15).

Figure 16:
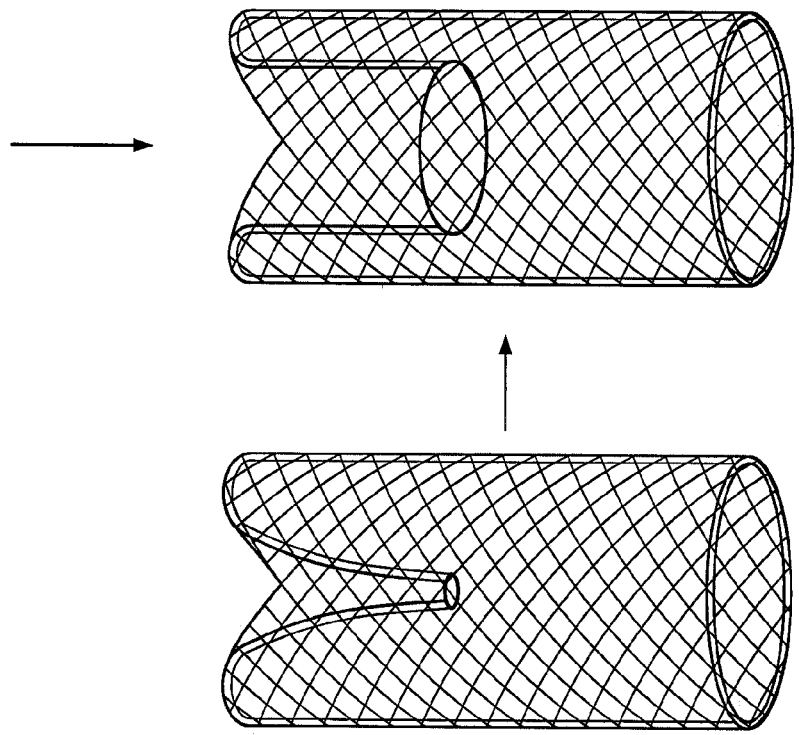
FIG. 16 shows a perspective view of a braided cylinder involuted inside itself to form an inner tube with a reduced diameter that acts as a one-way valve that opens under pressure.

In another embodiment, a braided tube is involuted inside itself and the inner tube forms a passively closed inner tube structure or one-way valve in part, due to the forces created by the involution of the braided tube (FIG. 16).

Figure 17:
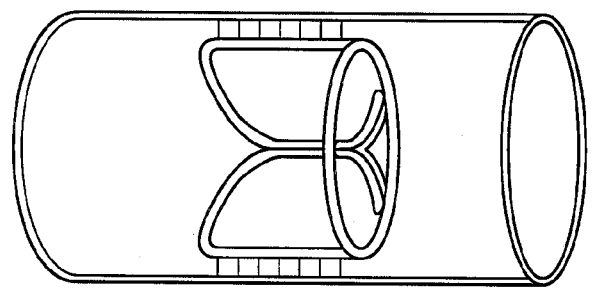
FIG. 17 shows a perspective view of an involution valve constructed with a cuff of material at either end.

In another embodiment, the involution valve may be formed by a double cylinder structure in which the innermost tube is folded inside the outermost tube (FIG. 17). In the previous discussion of the present invention, the outermost tube is folded inside itself. In this configuration, there can exist an additional cuff of tissue or scaffold at one or both ends of the valve construct. An additional cuff at the base of the valve would ease the surgical implantation of the valve by decreasing the risk of distorting the leaflets during suture placement since the leaflet are a distant from the sewing area at the cuff. The additional cuff(s) may be particularly useful for implantation of a pulmonic valve replacement and reconstruction of the right ventricular outflow tract.

Attachment

Figure 18:
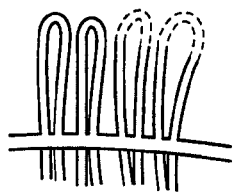
FIG. 18 shows material in a looped or tufted configuration.

One exemplary method of attachment of the inner wall (with or without flaps) to the outer wall is by using three or more "U" sutures (FIG. 13, referred to previously). Other techniques of attaching the inner to the outer wall of the valve include, but are not limited to, interlacing, interlocking, stapling, clipping, splicing, suturing, screwing, knitting, braiding, weaving, punching, tufting (see FIG. 18), stapling, gluing, welding, fusing, laminating and combinations thereof and the like.

Historically, tissue valves with leaflets secured by sutures failed due to the stress imposed at the sites of attachment. In the design of the present invention, the tissue has retained or imparted with healing capabilities that would theoretically offer reinforcement by enabling tissue growth and reinforcement at the suture sites.

Figure 19:
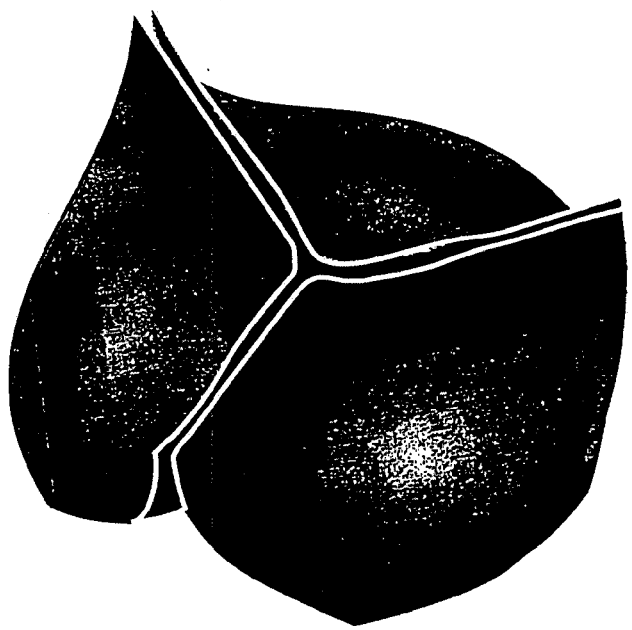
FIG. 19 shows a finite element analysis of the involution valve depicting an area of high stress at the attachment area of the inner and outer walls of the valve, with a gray scale such that high stress areas are shown in black and low stress are shown in white.

A mathematical stress analysis of the involution valve constructed of human blood vessel, indicated that an area of high stress would occur in a discrete area at each commissure (attachment area of the inner leaflets to the outermost wall) (see FIG. 19). In a dynamic model of the theoretical involution valve structure during the cardiac cycle, this area of high stress was noted to move its position along the wall during various phases of the cycle. In order to provide strength and dissipate this small area of high stress, an involution valve can be created with an area of attachment between the leaflets and outer wall as opposed to a line or point of attachment. As a more specific example, an involution valve can be constructed by weaving, knitting, or braiding the involution and attachment areas of the inner leaflets and outermost wall of the valve.

Interleaflet Triangles

Figure 20:
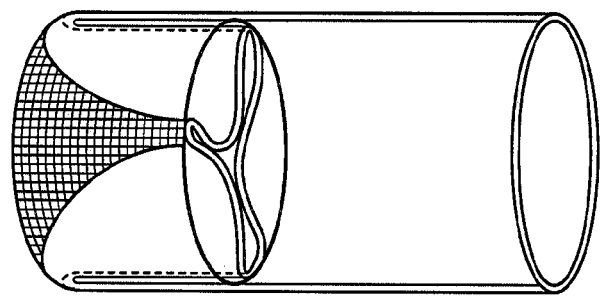
FIG. 20 shows a perspective view of the involution valve showing the attachment of the inner and outer tube by weaving them together in an interleaflet triangular pattern.

Native human semilunar valves have structures referred to as interleaflet triangles. These structures represent a triangular region between leaflets created by the angled attachment of the each leaflet to the wall. In the present invention, an analogous structure can be imposed in the involution valve by creating a triangular area of attachment of the leaflets to wall of the valve construct. This can be created by interlocking or interlacing the material with weaving, braiding or knitting techniques (FIG. 20).

In the native human semilunar valves the annulus (imaginary coronal circle representing the base of the valve) moves in opposition to the sinotubular junction (imaginary circle at the level of the leaflets most superior attachment to the wall or sinus) during the cardiac cycle. During diastole, the annulus increases diameter as the sinotubular junction decreases diameter. During systole, the reverse is true, namely, the annulus reduces diameter and the sinotubular junction increases diameter. This motion may be important for valve longevity and the sharing of stress between the leaflet and wall during the cycle. Inserting interleaflet triangles into the involution valve construct may help restore the opposing movement of the annulus with respect to the sinotubular junction. The alteration to the base of the valve construct to construct interleaflet triangles may permit independent movement of leaflets in relationship to one another.

In certain instances, the present invention is created from a tissue cylinder, in this case the interleaflet triangle can be re-approximated with a linear angle of sutures to relieve the point stress at the leaflet commissures. Angling of the base of each leaflet more closely approximates the normal anatomy and helps disperse the stress on the leaflet to a tapered row of sutures rather than a single point of attachment at each commissure.

Sinuses

In a human's native semilunar valve apparatus there exists a space between each leaflet and the vessel wall referred to as the Sinus of Valsalva. This space is known to increase the efficiency of valve function by providing an eddy current of circulating blood which functions, in part, to maintain the separation of the leaflet from the wall during the opening of the valve.

In the present invention, the outermost wall of the involuted cylinder valve construct can be purposefully enlarged at the base of the valve to recreate a potential space between the leaflet free edge and the outer wall. One exemplary method of creating the enlargement is to construct the valve such that the outermost wall is a larger diameter than the innermost wall cylinder. If the starting material is a tube, one way to achieve this is to use a conical shape of the material such that the smaller diameter of the cone will be involuted into the larger diameter of the cone.

Figure 21:
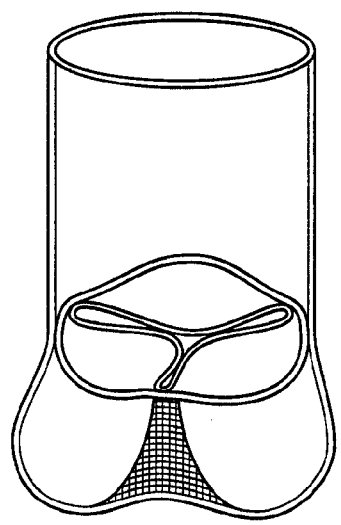
FIG. 21 shows a perspective view of the involution valve showing sinuses enlarged by providing excess material between the annulus and the sinotubular junction with the creation of interleaflet triangle by selectively weaving the inner tube to the outer tube between sinuses.

In more complicated methods of forming an involution valve, such as weaving, the sinuses can be integrated into the final geometry by creating selective pockets or outpouchings in the outer wall (see FIG. 21). Various techniques of weaving, knitting, and braiding can form pouches, pockets, pleats, corrugations, crimps and sinuses. Alternatively, portions of the outermost wall of the valve construct can be removed by incisions or scalloping to preserve a potential space (the native Sinus of Valsalva) to exist between the leaflet and the native aortic wall (FIG. 21).

Leaflet Modifications

Figure 22:
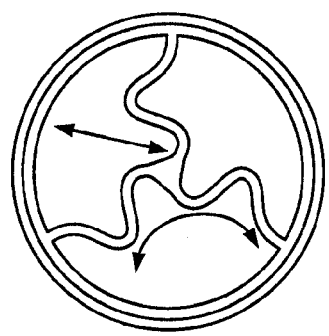
FIG. 22 shows a top view of the involution valve depicting excess leaflet material in the radial and circumferential directions.
Figure 23:
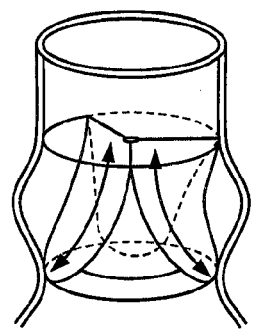
FIG. 23 shows a perspective view of the involution valve depicting excess leaflet material in the longitudinal plane.

As described previously, the native human semilunar valve leaflet ventricularis layer has gross corrugations of collagen and elastin in the radial direction which impart significant compliance in this orientation. In the circumferential direction, the fibrosa layer has a crimping of collagen that provides a counterforce to overextension of the leaflet during the period of more extreme loading-bearing (diastole). In order to more closely model the physical properties of the native human valve, the involution valve of the present invention may be constructed with excess material in the leaflet in the radial direction or circumferential directions. (FIG. 22). The techniques of fabricating the involution valve using knitting, weaving, or braiding of material are particularly useful, since excess material to create a "baggy" leaflet can be imparted during the sleeving process. Alternatively, excess material or pouches could be pleated during valve construction, particularly if the involution required folding of material. Using similar techniques, the leaflets of the involution valve can have excess material in the longitudinal direction (FIG. 23).

Modifications of the leaflets' shape by sculpturing the free edge may maximize leaflet coaptation (i.e., the adaptation or adjustment of parts to each other). Such alternative shape of leaflets include scalloping or rounding off the edges (concave). Other potential leaflet shapes are convex or bi-convex with formation of a central nodule by purposefully imparting a node shape at the midpoint. In certain cases, these shapes may better mimic native valve anatomy and help valve function.

Stents

Figure 24:
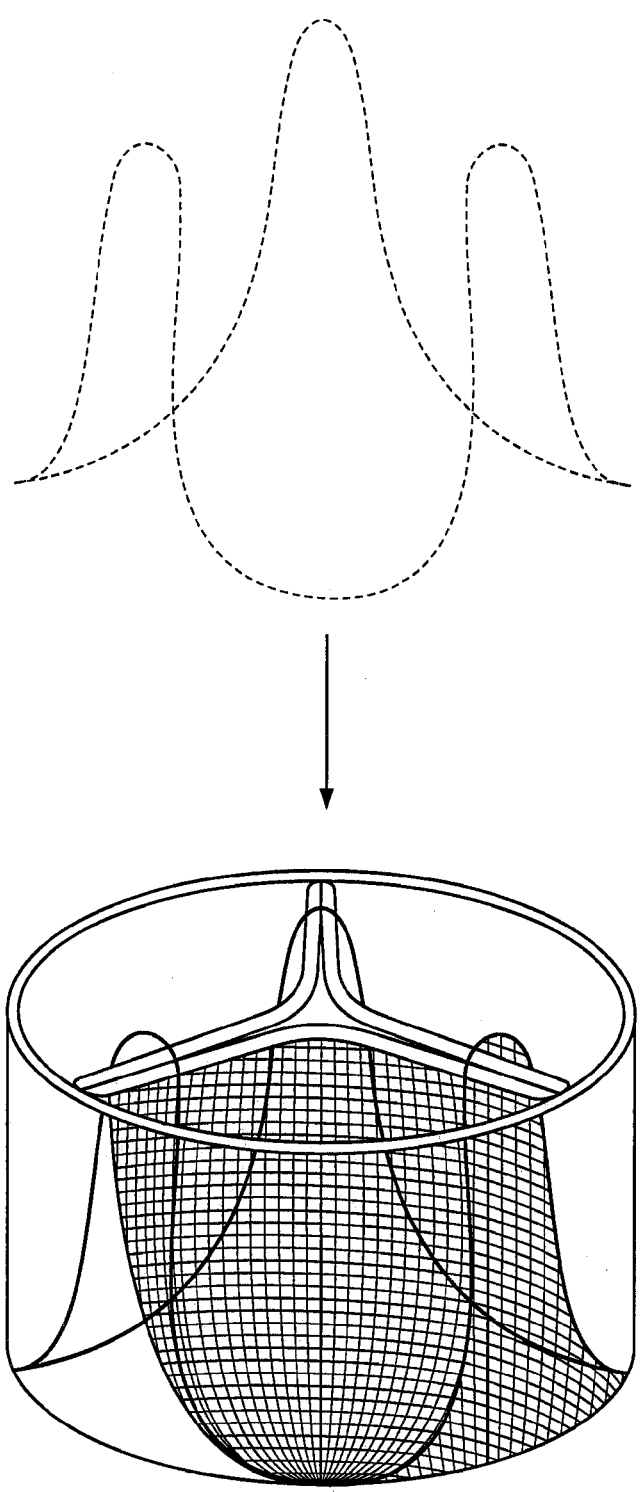
FIG. 24 shows a perspective view of the involution valve depicting the integration of a rigid or semi-rigid stent into the structure.

A sheet of woven, knitted, or braided material may be used in combination with a rigid or semi-rigid frame ("stent") to create a valve. The stent can function to hold the valve in the involuted position, which aids the surgeon in implantation. In another embodiment, a sheet of woven porcine (or other suitable source) decellularized small intestinal submucosa is suspended in a stent (FIG. 24).

Implantation

If the involuted cylinder valve formed by any of the aforementioned methods and materials is orientated such that following implantation, the most viable and anti-thrombogenic surface opposes the diastolic side (FIG. 1). The reason for this is that the highest mechanical stresses on the leaflets and greatest degenerative changes in tissues valves have been noted on the diastolic surface (i.e., the inflow surface). In the involution valve construct (if derived from a blood vessel), the endothelium is orientated towards the diastolic side since it since it may receive nutrients directly from the lumenal blood flow and most likely retains cellular repair capabilities.

As shown in FIG. 14 a design is provided for subcoronary implantation where the outer wall of the tissue cylinder is reduced between the three suture points to permit implantation below the coronary arteries when implanted into the aortic position.

Figure 25:
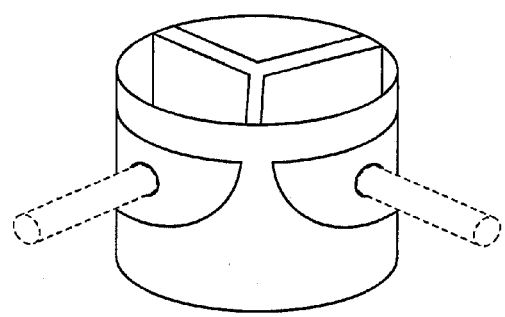
FIG. 25 shows a perspective view of the involution valve depicting the outer with cut away sections for coronary artery reimplantation intended for use with "inclusion" or "mini-root" valve implantation techniques; and, FIG. 26 shows a perspective view of the involution valve as collapsible braid depicting the ability of the structure to assume a reversible narrow endovascular insertion profile.

As shown in FIG. 25 the outer wall of tissue cylinder can remain intact and cut out for coronary artery re-implantation, inclusion or mini-root implantation.

Figure 26:
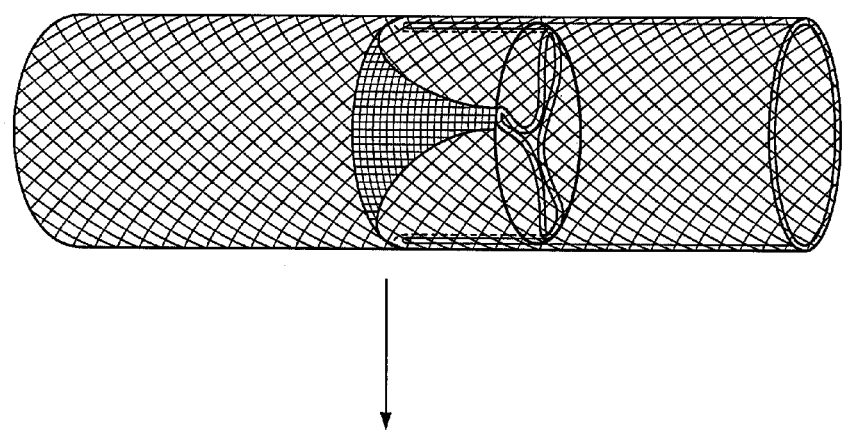

One advantage of a tubular braid configuration is the possibility of creating a tubular valve that is collapsible (FIG. 26). Braided tubes can be constructed which reduce diameter significantly when a longitudinal force is exerted on the tube. For example in one exemplary embodiment, the tubular valve is reduced in diameter by exerting a longitudinal force by a trocar on the inside of the tube, introduced into the endovascular space in minimally invasive manner, and is deployed as a larger diameter structure at the valve replacement site by removing the trocar.

Apparatus and methods for forming, inserting and using expandable and collapsible structures, e.g., cannulae, which may serve as an analogous technology useful for creating a scaffold capable of having a reduced diameter during implantation and expanding thereafter are disclosed in copending Patent Cooperation Treaty (designating the U.S.) application No. PCT/US02/40349, filed Dec. 16, 2002, entitled "DYNAMIC CANNULA".

Alternative Scaffolding Techniques

A mold of scaffold can be created by a tricuspid "ventricular" and "aortic" stamp (e.g., a silicone-coated aluminum mold). Thermoplastic scaffolding material is inserted between the two stamps to create the complex shape of the aortic root and valve.

Some scaffold materials (such as, but not limited to, P4HB) with thermoplastic properties can be welded instead of sutured at the commissures.

Computer-aided molecular deposition of scaffold material potentially be used in lithography to create the three-dimensional valve. The same process could generate a flat sheet, cylinder, or cylinder with three equidistant incisions (see the involuted cylinder method) which then undergo secondary folding to create a valve.

Special Processes

The present invention also contemplates the construction of a scaffold generally having the configuration made of a synthetic material, which is then used as a support on which to seed and grow cells. The basic concept of seeding is to transplant autologous cells onto a biocompatible and biodegradable scaffold that has been pre-formed in the three dimensional structure of a heart valve. The cells are attached to the scaffold while keeping tissues in vitro with physical signals to guide development of tissues. As the cells form extracellular matrix, the biodegradable polymer scaffold starts to degrade. The scaffold and the attached cells are implanted into the body where cells continue to produce matrix materials, providing increasing mechanical strength while the scaffold finishes its degradation (usually in about 6-8 weeks).

Possible culture additives include, but are not limited to, cytokines, growth factors, microencapsulated growth factors, heparin products, cell markers to track cells post-implantation, transfection vectors (e.g., green fluorescent protein), anti-microbial anti-fungal agents, mixtures thereof and the like.

Possible cells which can be used to seed the scaffold include, but are not limited to, fibroblasts, endothelial cells, myofibroblasts, smooth muscle cells, fetal-type smooth muscle cells, mixtures thereof and the like.

Cell sources include, but are not limited to, peripheral blood, human umbilical cord, blood, arteries (e.g., carotid), human foreskin, bone marrow, adipose tissue, mixtures thereof and the like.

Advantages

The involution valve can be constructed from a wide range of materials. The use of scaffolding materials (e.g., porcine small intestinal mucosa) offer the advantage of a potentially autologous living valve capable of growth and repair following maturation of the implant in the circulation.

The involution valve can being constructed as a braid, a knit, or a weave of material. The ability to fabricate the valve using these techniques enables the potential to create a valve with physical properties analogous to the native human leaflet. These techniques increase the potential strength and durability of the valve the reinforcement provided by interlacing the material at the attachment areas of the leaflet to the wall. It is advantageous that the involution valve can be constructed as a continuous structure using these techniques.

In contrast to previous attempts to reconstruct autologous arteries into valvular structures, the method described in this present invention enables a tri-leaflet valve to be constructed independent from its site of implantation. The valve may be transplanted to any desirable anatomical implant site. This reduces the technical challenge and allows the potential for pre-operative or intra-operative dynamic function testing prior to implantation. In certain instances, it is advantageous that the involution valve can assume a narrow profile and be deployed into the endovascular space by a minimally invasive means.

The involution valve can also be constructed from the patient's own tissues in an economical manner, offering an alternative treatment for valvular disease. If the valve retains its growth potential, it may be particularly useful for pulmonic valve substitution in the Ross procedure or in pediatric patients with congenital abnormalities of the pulmonary valve such as tetralogy of Fallot with absent valve syndrome.

The invention may also have applicability to non-medical application. The advantage of this design and method is the potential to create a valve with the following properties; large effective orifice area, a low pressure gradient, efficient closure velocity, and low regurgitation volume. The valve is suitable in rigid or non-rigid systems and wet or dry environments. The valve leaflets can potentially form a seal around an inner rod or piston. The valve can be constructed from a wide range of materials. The valve is potentially efficient and economical to construct and insert into the stream of flow. The invention will be further described in connection with the following examples, which are set forth for purposes of illustration only. Parts and percentages appearing in such examples are by weight unless otherwise stipulated.

EXAMPLES

Example 1

A tri-leaflet tissue valve can be constructed from the main pulmonary artery by the involution method and implanted into the aortic position in sheep (see experiment 1). This valve may also be suitable as a replacement for other valves (e.g., pulmonary valve).

Objective

An involuted cylinder valve constructed from pulmonary artery tissue and implanted in the aortic position in sheep.

Materials and Methods

From previously sacrificed donor swine (n=4, 50 kg+/−10 kg), the main pulmonary artery and its main left and right branches were harvested. The main pulmonary artery trunk was trimmed to create a tissue cylinder of height equal to the diameter of the recipient aortic annulus. $A=h\approx d$, where A=recipient aortic annulus diameter (mm), h=tissue cylinder height (mm), and d=tissue cylinder diameter (mm). Excess fat was trimmed from the specimen and adventitial layer was carefully peeled off as a single sheet of tissue and discarded. The tissue cylinder was incised with tree longitudinal incisions 120 degrees apart. $L=\frac{1}{2} h-2 t$, where L=incision length (mm), and t=wall thickness (mm) (see FIG. 1).

In two specimens, the edges of all three flaps of tissues were rounded-off along their free-edge, creating concave-shaped leaflets. In all constructs the flaps were involuted into the tissue cylinder and sutured to the cylinder wall at three equidistant points using "U" sutures (see FIGS. 2 and 3.). The outer wall of the valve construct was reduced between the three points to allow space for implantation of the valve inferior to the coronary arteries (see FIG. 4). In all cases, the valve was prepared in less than 20 minutes. Prior to implantation, the valve was inspected for competency by passive suspension of a column of saline.

A median sternotomy was performed and cardiopulmonary bypass was instituted in recipient sheep. Cold high potassium crystalloid cardioplegia was given by direct ostial cannulation. The ascending aorta was transversely transected 1 cm above the right coronary artery and native leaflets excised. The preformed valve construct was secured into the subcoronary position by interrupted 3-0 Tevdek™ sutures on the lower edge and a running 4-0 prolene along the superior aspect. The aortotomy was closed and the animal weaned from cardiopulmonary bypass. In animals that recovered cardiac function, echocardiography was performed to assess valve function.

Results

The two animals that received valve constructs without rounded-off leaflet free-edges displayed mild aortic regurgitation on two-dimensional echocardiography with continuous-wave Doppler using a hand-held epicardial probe. In the same group, the short-axis view exhibited coaptation of all three leaflets during valve closure. Symmetrical leaflet movement and good mobility was observed throughout the cardiac cycle in four-chamber apical view. A mean flow velocity of 2.49 m/sec was obtained in one animal with a 14 mm aortic annulus diameter. The two animals with rounded-off leaflet free edges had severe aortic insufficiency due to prolapse of two or all three leaflets and could not be weaned from bypass.

Conclusion

In this experiment, a segment of the main pulmonary artery was reconfigured into an aortic valve using a technique referred to as the "involuted cylinder" method and implanted into the subcoronary position in four sheep. In two constructs the leaflets were modified, creating concave leaflet free-edges. The modification was designed to eliminate deadspace at the base of the leaflets and reduce the risk of thrombosis formation. However, in these modified constructs the central region of the leaflets was not supported adequately which resulted in leaflet prolapse under diastolic load. The constructs without rounded leaflets assumed a more cup-like configuration and exhibited no prolapse, most likely due to the suspension of the leaflets at all points along the free-edge. It may also be significant that the longitudinal axis of the pulmonary artery wall becomes the radial axis of the valve leaflet. Increased extensibility of the leaflet in the radial direction may act to lessen the central orifice by providing more coaptation area

Example 2

A scaffold is constructed of decellularized porcine small intestinal submucosa. The involution method described above is used to form a functional three-dimensional valve. The valve is implanted into the individual and allowed to mature under in vivo conditions.

Objective

A Pulmonic Valve Replacement in Sheep Using an Involution Valve Constructed of Porcine Small Intestinal Submucosa Materials and Methods A sheet of 4-ply porcine small intestinal submucosa "SIS" (Cook, Inc.) of dimensions 68.2 mm long×20 mm wide was prepared. Two equidistant 8 mm long incisions were created extending from the free edge of the length to centerline of the material. The flat sheet was folded in half along the length with the smoother surface on the inside. A cylinder was formed by suturing the two free ends together with a running 7-0 prolene. The leaflets were secured in a perpendicular manner to the inner wall of the cylinder by "U" sutures. Two additional sheets of SIS were sutured to either end of the valve, creating two cylindrical cuffs of tissues at either end of the valve construct.

A median sternotomy was performed and cardiopulmonary bypass was instituted in a recipient sheep. Cold high potassium crystalloid cardioplegia was given by ascending aortic cannulation. The pulmonary artery was clamped and transected one millimeter above the pulmonary valve. The native pulmonary valve was excised. The preformed valve construct was secured at the superior aspect to the distal pulmonary trunk using 5-0 prolene. The cuff at the base of the valve was sutured to the proximal remnant of the pulmonary trunk Protomine™ was given and the animal was weaned from cardiopulmonary bypass. The animal recovered cardiac function and echocardiography was performed to assess valve function.

Results

The animal was successfully weaned from bypass. The pulmonary valve replacement displayed no pulmonic regurgitation on two-dimensional echocardiography with continuous-wave Doppler using a hand-held epicardial probe. The short-axis view exhibited coaptation of all three leaflets during valve closure. Symmetrical leaflet movement and good mobility was observed throughout the cardiac cycle in four-chamber apical view.

Conclusion

An involution valve constructed from decellularized porcine small intestinal submucosa functioned as a trileaflet pulmonary artery replacement in an acute sheep model. Chronic studies are necessary to determine the ability of the scaffold material to endothelialize and populate with autologous cells following endovascular implantation. Further investigation as to the function of the valve following implantation will help determine its usefulness in patients.

Example 3

A sheet of the patient's pericardium is harvested and formed into a valve construct using the involution method as described hereinabove at the surgical backtable. The valve construct is tested, then reimplanted into the same patient as a living autologous valve replacement.

Example 4

Formation of Scaffold

An unwoven polyglycolic acid ("PGA") mesh sheet 24 mm×75 mm and 1.5 mm thick is prepared and rolled into a cylinder. Three equidistant longitudinal 10 mm incisions are used to create three flaps which are involuted inside the cylinder and secured 120 degrees apart to form commissures. Scallop-shaped segments of the outermost wall of the cylinder are removed between the commissures to form the scaffold.

Example 5

Seeding

The scaffold of Example 4 created of a material that will support cellular growth, e.g., celluloid. Peripheral blood is harvested, samples are spun in column and cells are recovered (e.g., circulating endothelial cells) which are then serial plated on fibronectin culture plates and allowed to expand (e.g., static growth for 1 week). Cells are then seeded onto a celluloid construct in a rotating, pulsatile, or continuous flow bioreactor for a period of time (e.g., 4 weeks), then the valve is implanted in the patient to continue to mature, differentiate, and evolve in vivo.

Example 6

A valve is created by any of the examples or methods discussed hereinabove and temporarily implanted in the body (endovascular or other site) to allow maturation. For instance, the valve can be deployed using a minimally invasive apparatus into the descending aorta, exposed to the blood stream and mechanical stresses of the cardiac cycle for a period of weeks, and then removed from the body and reimplanted as a permanent valve replacement.

Example 7

A valve is created by any of the examples or methods discussed hereinabove and implanted in the endovascular space using a minimally invasive means.

It will be understood that the terms "a" and "an" as used herein are not intended to mean only "one," but may also mean a number greater than "one." All patents, applications and publications referred to herein are hereby incorporated by reference in their entirety. While the invention has been described in connection with certain embodiments, it is not intended to limit the scope of the invention to the particular forms set forth, but, on the contrary, it is intended to cover such alternatives, modifications, and equivalents as may be included within the true spirit and scope of the invention as defined by the appended claims.

The invention claimed is:

1. A method of forming a prosthetic valve, comprising:
   a. providing a tube of material having an inner wall, an outer wall, a diameter "d", a height "h" and a wall thickness "t";
   b. cutting three longitudinal incisions from one end in said material about 120 degrees apart to form three flaps, each said flap having a first edge, a second edge generally parallel to said first edge, and a bottom edge;
   c. involuting each said flap within said tube; and,
   d. attaching each said first edge and second edge of each involuted flap to said inner wall of said tube.

2. The method of claim 1, wherein said three longitudinal incisions have a length "L", such that L=½h−2t, where "h" is the tube height and "t" is the thickness of said tube.

3. The method of claim 1, wherein said height "h" is approximately equal to a diameter of a recipient aortic annulus diameter "A".

4. The method of claim 1, wherein the first, bottom, or second edges, or any combination therefore, of each flap are cut to be rounded off to create concave shaped leaflets.

5. The method of claim 1, wherein scallop shaped segments of said outer tube wall are removed between commissures.

6. The method of claim 1, wherein said attaching is achieved by any one or more of suturing, interlacing, interlocking, stapling, clipping, splicing, screwing, knitting, braiding, weaving, punching, tufting, gluing, welding, fusing, and laminating.

7. The method of claim 1, wherein said tube is comprises a generally rectangular sheet of material that has two opposing sides joined together.

8. An endovascular valve, comprising:
   a. a flexible tube of material comprising a first end and a second end, an inner wall, and an outer wall; and
   b. a plurality of leaflets formed from a portion of said first end by making a plurality of longitudinal incisions in said second end to form a plurality of flaps, each flap having a first edge and second edge, involuting said flaps toward said inner wall and securing said first edge and second edge of each flap to said inner wall of said tube.

9. The method of claim 1, wherein said attaching is achieved by any one or more of suturing, stapling, and gluing.

10. The method of claim 1, wherein said attaching is achieved by suturing.

11. The valve of claim 8, wherein the material comprises a synthetic material.

12. The valve of claim 8, wherein the material comprises one or more of a polyglycolic acid, a polyhydroxyalkanote, a polylactic acid, a polycaprolactone, a fibrin gel, poly-4-hydroxybutyrate, a hydrogel, a polyester, a metal, and a nitinol.

13. The valve of claim 11, wherein the material comprises one or more of polyglycolic acid, polylactic acid, and poly-4-hydroxybutyrate.

14. The valve of claim 8, wherein the material comprises an organic material.

15. The valve of claim 14, wherein the organic material comprises one or more of a polypropylene, a polyester, a silk, a nylon, a rubber, a silicone, a cellulosic material, a polytetrafluoroethylene, and a polyurethane.

16. The valve of claim 14, wherein the organic material comprises one or more of a polypropylene, a nylon, a silicone, and a polyurethane.

17. The valve of claim 8, wherein the material comprises a biological material.

18. The valve of claim 17, wherein the biological material comprises one or more of a pericardial tissue, an artery, a vein, a portion of a gastrointestinal tract, and a portion of an intestinal submucosa.

19. The valve of claim 17, wherein the biological tissue comprises one or more of an artery or a vein.

20. The valve of claim 17, wherein the biological material is decellularized.

21. The valve of claim 17, wherein the biological material comprises porcine tissue.

22. The valve of claim 17, wherein the biological material comprises human tissue.

* * * * *

UNITED STATES PATENT AND TRADEMARK OFFICE
CERTIFICATE OF CORRECTION

PATENT NO. : 7,331,993 B2  Page 1 of 1
APPLICATION NO. : 10/512005
DATED : February 19, 2008
INVENTOR(S) : Jennifer White It is certified that error appears in the above-identified patent and that said Letters Patent is hereby corrected as shown below:

Col. 1, line 14, insert the following:

-- FEDERALLY SPONSORED RESEARCH OR DEVELOPMENT

This invention was made with Government support under Grant No. DAMD17-99-2-9001 awarded by the U.S. Department of the Army. The Government has certain rights in the invention. --

Signed and Sealed this

Seventeenth Day of August, 2010

David J. Kappos
*Director of the United States Patent and Trademark Office*